US00PP30063P3

(12) United States Plant Patent
Finn

(10) Patent No.: US PP30,063 P3
(45) Date of Patent: Jan. 8, 2019

(54) BLACKBERRY PLANT NAMED 'HALL'S BEAUTY'

(50) Latin Name: ***Rubus* subg. *Rubus* Watson.**
Varietal Denomination: Hall's Beauty

(71) Applicant: The United States of America, as Represented by the Secretary of Agriculture, Washington, DC (US)

(72) Inventor: Chad E. Finn, Corvallis, OR (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 29 days.

(21) Appl. No.: 15/530,950

(22) Filed: Mar. 28, 2017

(65) Prior Publication Data

US 2018/0288915 P1 Oct. 4, 2018

(51) Int. Cl.
*A01H 5/08* (2018.01)
*A01H 6/74* (2018.01)

(52) U.S. Cl.
USPC ..... Plt./203
CPC ..... *A01H 6/7499* (2018.05)

(58) Field of Classification Search
USPC ..... Plt./156, 203
See application file for complete search history.

*Primary Examiner* — Susan McCormick Ewoldt
*Assistant Examiner* — Karen M Redden
(74) *Attorney, Agent, or Firm* — John Fado; Gail Poulos

(57) ABSTRACT

A new and distinct blackberry cultivar that originated from seed produced from a cross between the female blackberry plant 'NZ 9629R-1' (unpatented) and the male parent blackberry plant 'ORUS 1939-4' (unpatented). This new blackberry cultivar can be distinguished by its very large, many petaled, and attractive flowers, medium to high yields of large and very sweet flavored berries with good firmness and color and that are early ripening, and the trailing plant is completely thornless.

4 Drawing Sheets

Latin name of the genus and species of the plant claimed: 'HALL'S BEAUTY' is a blackberry plant that is *Rubus* subg. *Rubus* Watson.

Variety denomination: The new blackberry plant claimed is of the variety denominated 'Hall's Beauty' *Rubus* subg. *Rubus* Watson.

BACKGROUND OF THE INVENTION

The present invention relates to a new and distinct blackberry cultivar designated 'Hall's Beauty' and botanically known as *Rubus* subg. *Rubus* Watson. This new blackberry cultivar was discovered in Corvallis, Oreg. in July 2008 and originated from a cross between the female blackberry plant 'NZ 9629R-1' (unpatented) and the male parent blackberry plant 'ORDS 1939-4' (unpatented). 'Hall's Beauty's spinelessness is derived from 'Lincoln Logan' (unpatented) that can be found as a parent four and five generations back in 'Hall's Beauty's pedigree. The original seedling of the new cultivar was asexually propagated at a nursery in Benton County, Oreg. The new cultivar was established in vitro from a cane cutting and microcuttings have been taken and rooted from this sort of culture. The present invention has been found to be stable and reproduce true to type through successive asexual propagations.

SUMMARY OF THE INVENTION

The following are the most outstanding and distinguishing characteristics of this new cultivar when grown under normal horticultural practices in Oregon. 1. A high plant vigor as compared to 'Black Diamond' (unpatented); 2. Trailing growth habit; 3. Early date for 50% of ripe fruit compared to 'Black Diamond' (unpatented) and 'Marion'

(unpatented); 4. Weight of fruit is heavier compared to 'Marion' (unpatented) and similar to 'Columbia Star' (U.S. Plant Pat. No. 25,532); 5. Fruit are sweeter (higher soluble solids) than 'Black Diamond' (unpatented), 'Columbia Star' (U.S. Plant Pat. No. 25,532), and 'Marion' (unpatented); 6. Flowers are much larger in diameter, with many more petals per flower, than those of the commercial cultivars 'Black Diamond' (unpatented), 'Columbia Star' (U.S. Plant Pat. No. 25,532), and 'Marion' (unpatented).

BRIEF DESCRIPTION OF THE PHOTOGRAPHS

This new blackberry plant is illustrated by the accompanying photographs that show the flowers, fruit and entire plants; the colors shown are as true as can be reasonably obtained by conventional photographic procedures.

Figure 1:
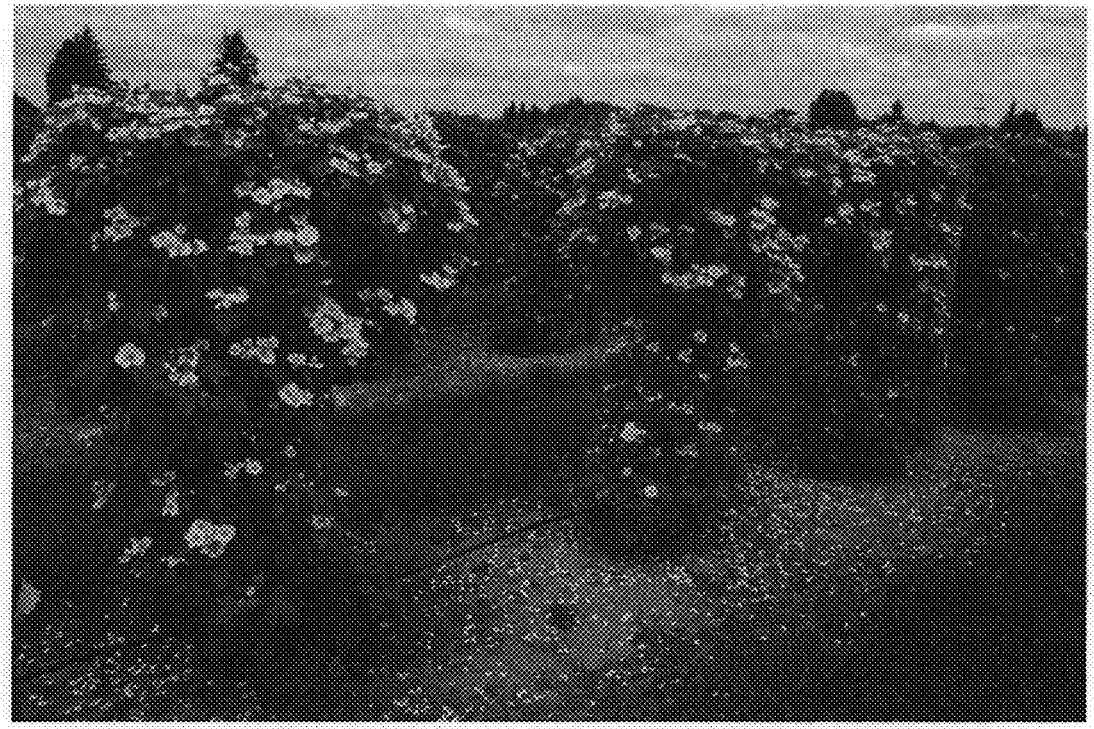

FIG. 1. shows an entire 3-year old plant in bloom. As is typical for commercial production, trailing primocanes are lifted from the ground in late summer and tied to a two wire trellis with the lower wire approximately 1.0 m above the ground and the upper wire approximately 1.5 m above the ground.

Figure 2:
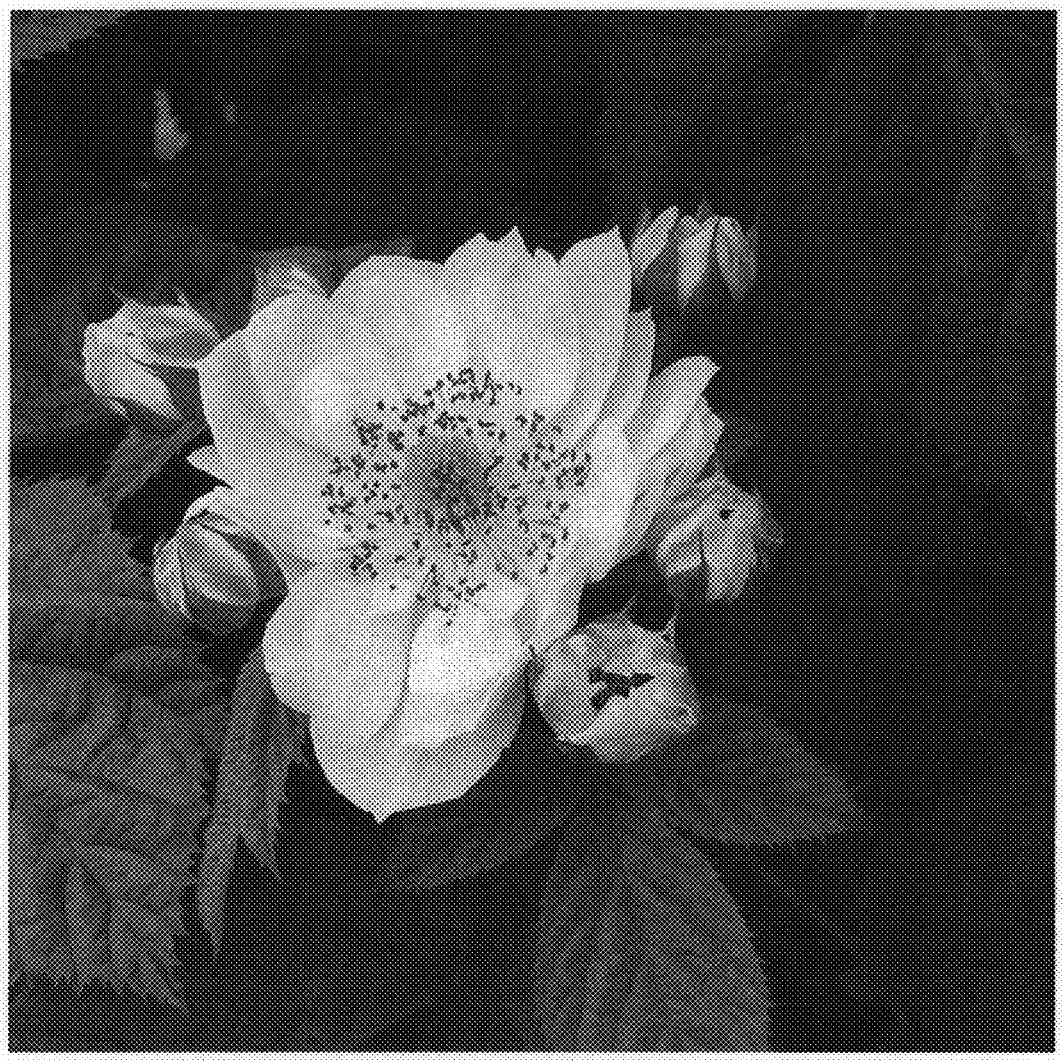

FIG. 2. shows a typical flowering cluster in bloom.

Figure 3:
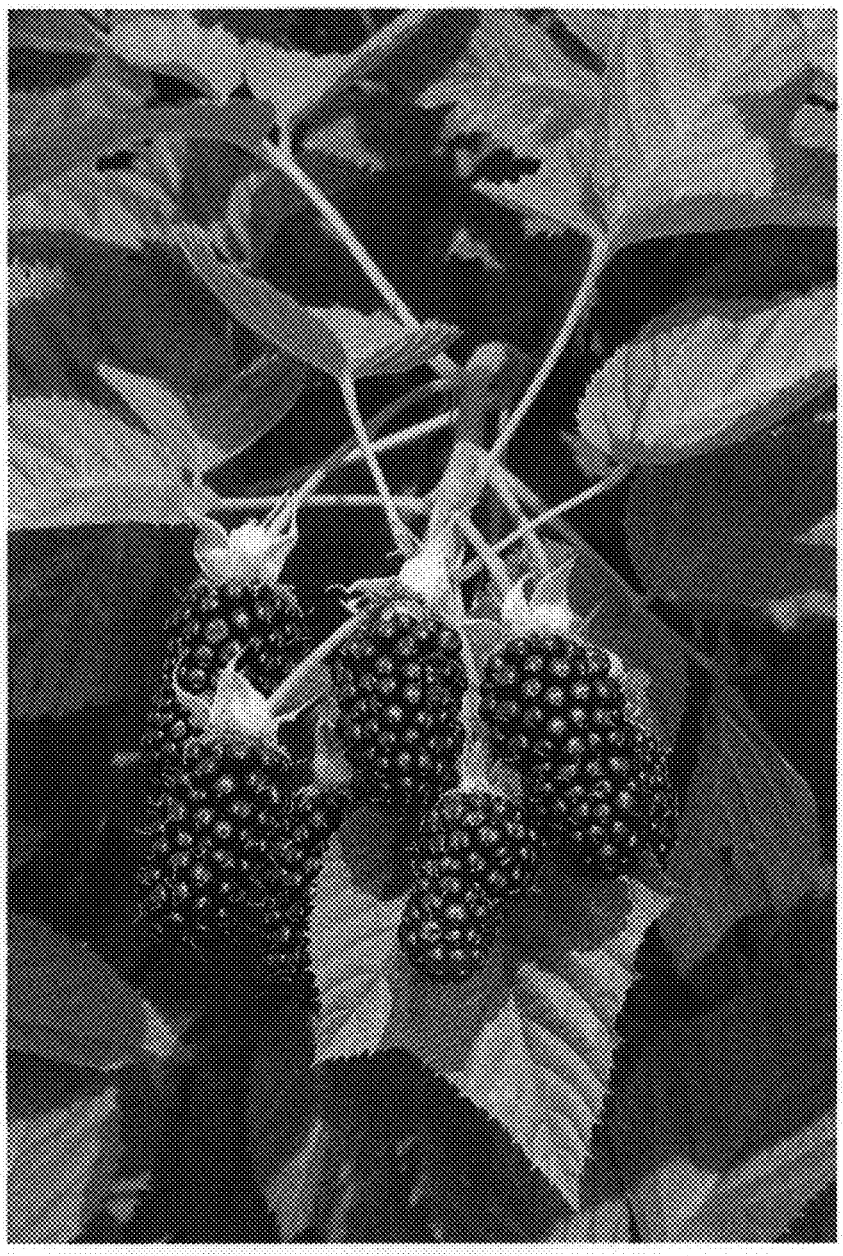

FIG. 3. shows typical fruiting cluster with ripe fruit 'Hall's Beauty'.

Figure 4:
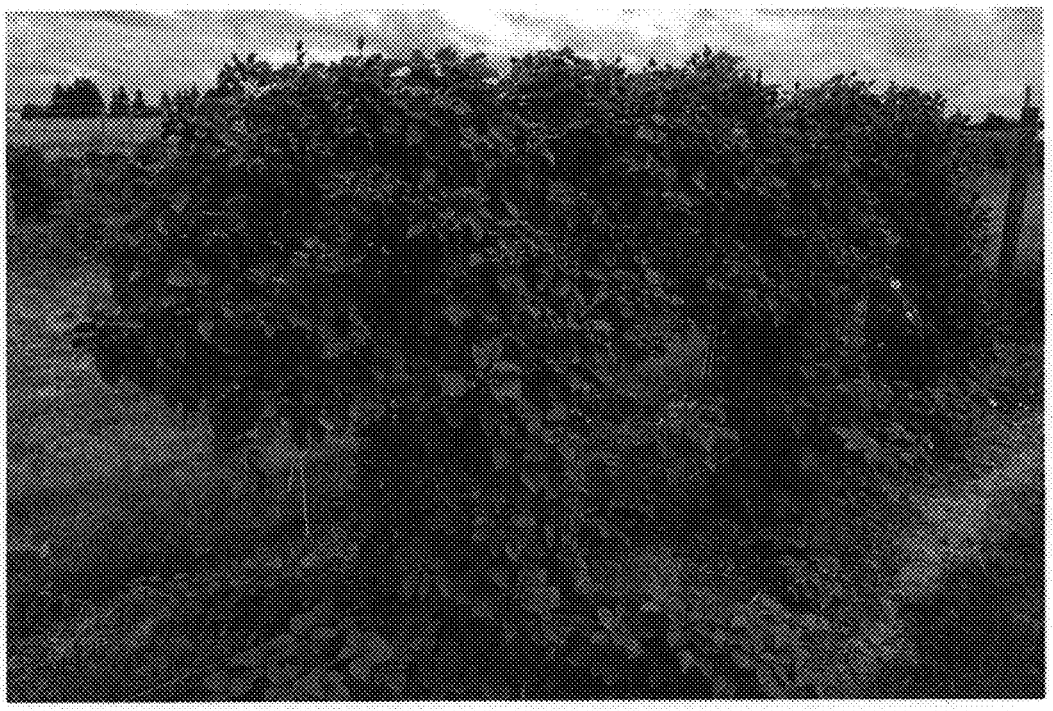

FIG. 4. shows an entire fruiting 4-year old plant. As is typical for commercial production, trailing primocanes are lifted from the ground in late summer and tied to a two wire trellis with the lower wire approximately 1.0 m above the ground and the upper wire approximately 1.5 m above the ground.

DETAILED DESCRIPTION OF THE NEW CULTIVAR

The following description of 'Hall's Beauty' is based on observations taken from 2012 to 2016 growing seasons in trials in Corvallis and Aurora, Oreg. This description is in accordance with UPOV terminology. Color designations, color descriptions and other phenotypical descriptions may deviate from the stated values and descriptions depending upon variation in environmental, seasonal, climatic and cultural conditions. 'Hall's Beauty' has not been observed under all possible environmental conditions. Color terminology follows The Royal Horticultural Society Colour Chart. London (R.H.S.) ($5^{th}$ edition, 2007).

Table 1 shows important characteristics of the new cultivar. Characteristics include plant vigor, growth habit, date of full bloom, flower diameter, number of flower petals per flower, date 50% of fruit were ripe, weight of primary fruit, soluble solids and winter tolerance in Aurora, Oreg. (45° 16' 49" N/122° 44' 50" W).

TABLE 1

| Characteristic | 'Hall's Beauty' |
|---|---|
| Plant vigor | High compared to 'Black Diamond' |
| Growth habit | Trailing |
| Date full bloom | 5 May, early compared to 'Marion' |
| Flower diameter | 4.87 cm (much wider than 'Black Diamond', 'Columbia Star' and 'Columbia Sunrise' (U.S. Plant Pat. No. 29,367)) |
| Number of flower petals per flower | 15.17 |
| Date 50% of fruit were ripe | 18 June (early compared to 'Black Diamond' and 'Marion') |
| Weight of primary fruit | 6.26 g (larger than 'Marion', similar to 'Columbia Star') |
| Soluble solids (%; in Brix) | 15.37 (higher than 'Black Diamond', 'Columbia Star', and 'Marion') |
| Winter tolerance in Aurora, Oregon (45° 16' 49" N/122° 44' 50" W) | Good (similar to 'Marion') |

Table 2 shows floricane and mature primocane characteristics of the new cultivar. Characteristics include diameter at base, diameter at midpoint, diameter at terminus, internode length at base, internode length at midpoint, internode length at terminus, presence of spines further than 0.6 m from the soil surface, presence of spines less than 0.6 m from the soil surface, floricane color at base, floricane color at midpoint, floricane color at terminus, floricane lateral length, floricane lateral strength, primocane color at base, primocane color at midpoint, primocane color at terminus, floricane length, and floricane length (range).

TABLE 2

| Characteristic | 'Hall's Beauty' |
|---|---|
| Diameter at base | 1.04 cm |
| Diameter at midpoint | 0.97 cm |
| Diameter at terminus | 0.19 cm |
| Internode length at base | 6.82 cm |
| Internode length at midpoint | 5.05 cm |
| Internode length at terminus | 1.96 cm |
| Presence of spines further than 0.6 m from the soil surface | Absent |
| Presence of spines less than 0.6 m from the soil surface | Absent |
| Floricane color at base | Mottled green (152A) and red (183A) |
| Floricane color at midpoint | Green (152D), streaked and mottled with red (178B) |
| Floricane color at terminus | Green (N144A), streaked with red (178B) |
| Floricane lateral length | Medium-long |
| Floricane lateral strength | Medium-strong |
| Primocane color at base | Green (146C) |

TABLE 2-continued

| Characteristic | 'Hall's Beauty' |
|---|---|
| Primocane color at midpoint | Green (144A) |
| Primocane color at terminus | Green (147C) |
| Floricane length | 2.91 m |
| Floricane length (range) | 2.21-4.05 m |

Table 3 shows primocane foliage characteristics of the new cultivar. Primocane characteristics include mature compound leaf width, mature compound leaf length, number of leaflets per primocane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, spine presence on leaves, pubescence on primocane leaflet: upper surface, pubescence on primocane leaflet: undersurface, primocane leaf color abaxial, primocane leaf color adaxial, petiole length, petiole color: upper surface, petiole color: undersurface, petiolule length: terminal leaflet, petiolule length: first distal leaflet, petiolule color: abaxial, petiolule color: adaxial, stipule length, stipule width, and stipule attitude.

TABLE 3

| Characteristic | 'Hall's Beauty' |
|---|---|
| Mature compound leaf width | 21.22 cm |
| Mature compound leaf length | 18.18 cm |
| Number of leaflets per primocane compound leaf | 5.00 |
| Mature leaflet shape | Compound, odd-pinnate. Terminal leaflet often 3-lobed |
| Mature leaflet apex | Broadly acute |
| Mature leaflet base | Cordate |
| Mature terminal leaflet width | 10.80 cm |
| Mature terminal leaflet length | 11.57 cm |
| Mature first lateral leaflet width | 6.97 cm |
| Mature first lateral leaflet length | 9.70 cm |
| Leaflet margin | Doubly serrate |
| Leaflet serration teeth length | 0.23 cm |
| Leaflet serration teeth width at base | 0.21 cm |
| Spine presence on leaves | No |
| Pubescence on primocane leaflet: upper surface | Yes, light |
| Pubescence on primocane leaflet: undersurface | Yes, light |
| Primocane leaf color abaxial | Green (137B) |
| Primocane leaf color adaxial | Green (138B) |
| Petiole length | 6.67 |
| Petiole color: upper surface | Green (138B) |
| Petiole color: undersurface | Green (144B) |
| Petiolule length: terminal leaflet | 2.41 cm |
| Petiolule length: first distal leaflet | 1.15 cm |
| Petiolule color: abaxial | Green (138B) with blush of red (178A) |
| Petiolule color: adaxial | Green (144C) |
| Stipule length | 1.53 cm |
| Stipule width | 0.17 cm |
| Stipule attitude | Very erect and parallel to stem, crossed |

Table 4 shows floricane foliage characteristics of the new cultivar. Floricane characteristics include mature compound leaf width, mature compound leaf length, number of leaflets per floricane compound leaf, mature leaflet shape, mature leaflet apex, mature leaflet base, mature terminal leaflet width, mature terminal leaflet length, mature first lateral leaflet width, mature first lateral leaflet length, leaflet margin, leaflet serration teeth length, leaflet serration teeth width at base, pubescence on floricane leaflet: upper surface, pubescence on floricane leaflet: undersurface, floricane leaf color abaxial, floricane leaf color adaxial, petiole length, petiolule length: terminal leaflet, petiolule length: first distal leaflet, petiolule color: abaxial, petiolule color: adaxial, stipule length, and stipule width.

TABLE 4

| Characteristic | 'Hall's Beauty' |
|---|---|
| Mature compound leaf width | 10.17 cm |
| Mature compound leaf length | 9.50 cm |
| Number of leaflets per floricane compound leaf | 2-5, typically 3 |
| Mature leaflet shape | Ovate |
| Mature leaflet apex | Broadly acuminate |
| Mature leaflet base | Ovate |
| Mature terminal leaflet width | 4.62 cm |
| Mature terminal leaflet length | 6.32 cm |
| Mature first lateral leaflet width | 4.23 cm |
| Mature first lateral leaflet length | 5.97 cm |
| Leaflet margin | Doubly serrate |
| Leaflet serration teeth length | 0.22 cm |
| Leaflet serration teeth width at base | 0.31 cm |
| Pubescence on floricane leaflet: upper surface | Yes, light and short |
| Pubescence on floricane leaflet undersurface | Yes, medium density, short |
| Floricane leaf color abaxial | Green (137C) |
| Floricane leaf color adaxial | Green (147B) |
| Petiole length | 6.30 cm |
| Petiole color adaxial | Green (144B) |
| Petiole color abaxial | Green (144C) |
| Petiolule length terminal leaflet | 2.03 cm |
| Petiolule length first distal leaflet | 2.37 cm |
| Petiolule color abaxial | Green (144B) |
| Petiolule color adaxial | Green (144C) |
| Stipule length | 1.00 cm |
| Stipule width | 0.09 cm |

Table 5 shows flower and flowering characteristics of the new cultivar. Flower and flowering characteristics include date 1st bloom, date full bloom, date last bloom, petal color, number flowers per cluster, number of petals per flower, flower diameter, petal length, petal width, and number of sepals per flower.

TABLE 5

| Characteristic | 'Hall's Beauty' |
|---|---|
| Date 1st bloom | 28-Apr |
| Date full bloom | 5-May |
| Date last bloom | 19-May |
| Petal color | White (NN155C) |
| Number flowers per cluster | 6.50 |
| Number of petals per flower | 15.17 |
| Flower diameter | 4.87 cm |
| Petal length | 2.10 cm |
| Petal width | 1.60 cm |
| Number of sepals per flower | 5.00 cm |
| Peduncle length | 11.32 cm |
| Rachis length | 5.73 cm |
| Peduncle color | Green (146C), sometimes flushed with red (173A to 182A) |
| Cyme type | Elongate simple cyme |

Table 6 shows fruit and fruiting characteristics of the new cultivar. Fruit and fruiting characteristics include date 5% of fruit were ripe, date 50% of fruit were ripe, date 95% of fruit were ripe, weight of primary fruit, weight of secondary fruit, diameter of primary fruit at equator, diameter of 2° fruit at equator, diameter of 1° fruit at poles: tip, diameter of 1° fruit at poles: base, diameter of 2° fruit at poles: tip, diameter of 2° fruit at poles: base, berry length 1° fruit, berry length 2° fruit, ratio of primary fruit length to width, shape description, uniformity of berry shape, color when full ripe, number of drupelets per fruit, individual seed weight, glossiness, firmness, flavor, texture of fruit when chewed, drupelet skin resistance to abrasion, ease of separation of fruit from pedicel, machine harvestability, resistance to heat damage of fruit, berries per inflorescence—mean, berries per inflorescence range, soluble solids (%; in Brix), pH, titratable acidity (% as citric acid), and yield (actual kg·plt−1).

TABLE 6

| Characteristic | 'Hall's Beauty' |
|---|---|
| Date 5% of fruit were ripe | 15 June |
| Date 50% of fruit were ripe | 19 June |
| Date 95% of fruit were ripe | 6 July |
| Weight of primary fruit | 6.26 g |
| Weight of secondary fruit | 5.58 g |
| Diameter of primary fruit at equator | 1.75 g |
| Diameter of 2° fruit at equator | 1.73 cm |
| Diameter of 1° fruit at poles: tip | 1.05 cm |
| Diameter of 1° fruit at poles: base | 1.51 cm |
| Diameter of 2° fruit at poles: tip | 1.07 cm |
| Diameter of 2° fruit at poles: base | 1.57 cm |
| Berry length primary fruit | 3.10 cm |
| Berry length 2° fruit | 2.87 cm |
| Ratio of primary fruit length to width | 1.78 |
| Shape description | Conical |
| Uniformity of berry shape | Excellent |
| Color when full ripe | Black (203C) |
| Number of drupelets per fruit | 91.17 |
| Total seed weight per fruit | 180.5 mg |
| Individual seed weight | 1.99 mg |
| Glossiness | Medium |
| Firmness | Moderate |
| Flavor | Excellent, sweet |
| Texture of fruit when chewed | Excellent |
| Drupelet skin resistance to abrasion | Very good |
| Ease of separation of fruit from pedicel | Easy |
| Machine harvestability | Excellent |
| Resistance to heat damage of fruit | Good |
| Berries per inflorescence - mean | 6.78 |
| Berries per inflorescence range | 6-8 |
| Soluble solids (%; in Brix) | 15.37 |
| pH | 3.26 |
| Titratable acidity (% as citric acid) | 12.47 |
| Yield (actual kg · plt − 1) | 7.72 |
| Disease response | Under a typical, minimal, disease management program does not exhibit any particular disease problems |

COMPARISON WITH PARENTAL AND COMMERCIAL CULTIVARS

'Hall's Beauty' differs from the female parent 'NZ 9629R-1' (unpatented) in that 'Hall's Beauty' has large-sized, glossy, fruit (6.3 g), while 'NZ 9629R-1' has slightly pubescent fruit that are smaller (4.5 g).

'Hall's Beauty' differs from the male parent blackberry plant 'ORDS 1939-4' (unpatented) in that it is spineless, has conic, glossy and sweet berries and moderate to high yields, while 'ORDS 1939-4' (unpatented) is spiny and has barrel shaped pubescent berries, and moderate yields.

'Hall's Beauty' flowers are much larger in diameter, with many more petals per flower, than those of the commercial cultivars 'Black Diamond' (unpatented), 'Columbia Star' (U.S. Plant Pat. No. 25,532) and 'Marion' (unpatented).

'Hall's Beauty' differs from 'Marion' (unpatented) in that 'Hall's Beauty' is spineless, early ripening and has medium-large (6.3 g), firm fruit while 'Marion' (unpatented) is spiny and ripens the crop in midseason and has medium yields of medium sized (5.0 g) and soft fruit that are unevenly shaped. 'Hall's Beauty' differs from the commercial cultivar 'Black Diamond' (unpatented) in that 'Hall's Beauty' carries the 'Lincoln Logan' (unpatented) source of spinelessness and therefore the canes are completely spineless and the plants are vigorous with medium-large (6.3 g) fruit that are an excellent, sweet, aromatic flavor, while 'Black Diamond' (unpatented) carries the 'Austin Thornless' (unpatented) source of spinelessness and so has spines on the base of the canes and the plants are not vigorous and they produce smaller (5.2 g) fruit with a mild flavor. 'Hall's Beauty' further differs from the commercial cultivars 'Black Diamond' (unpatented), 'Marion' (unpatented) and 'Columbia Star' (U.S. Plant Pat. No. 25,532) based on having sweeter (high soluble solids) fruit.

'Hall's Beauty' is primarily suited to the machine-harvested, processed-fruit market but is also firm enough for fresh market sales and the large, attractive flowers make it a potential ornamental for homeowners.

I claim:

1. A new and distinct cultivar of blackberry plant, substantially as illustrated and described, characterized by its very large, many petaled, and attractive flowers, medium to high yields of large and very sweet flavored berries with good firmness and color and that are early ripening, and the trailing plant is completely thornless.

* * * * *